(12) United States Patent
Takagi et al.

(10) Patent No.: US 8,337,083 B2
(45) Date of Patent: Dec. 25, 2012

(54) IMAGING DEVICE

(75) Inventors: Shin-ichiro Takagi, Hamamatsu (JP);
Kazuhisa Miyaguchi, Hamamatsu (JP)

(73) Assignee: Hamamatsu Photonics K.K.,
Hamamatsu-shi, Shizuoka (JP)

( * ) Notice: Subject to any disclaimer, the term of this patent is extended or adjusted under 35 U.S.C. 154(b) by 164 days.

(21) Appl. No.: 12/682,632

(22) PCT Filed: Oct. 14, 2008

(86) PCT No.: PCT/JP2008/068574
§ 371 (c)(1),
(2), (4) Date: Apr. 28, 2010

(87) PCT Pub. No.: WO2009/051103
PCT Pub. Date: Apr. 23, 2009

(65) Prior Publication Data
US 2010/0220839 A1 Sep. 2, 2010

(30) Foreign Application Priority Data
Oct. 16, 2007 (JP) ................................ P2007-269467

(51) Int. Cl.
*A61B 6/14* (2006.01)
(52) U.S. Cl. ........................................ 378/191; 378/189
(58) Field of Classification Search .................. None
See application file for complete search history.

(56) References Cited

U.S. PATENT DOCUMENTS

| | | | |
|---|---|---|---|
| 5,691,539 A * | 11/1997 | Pfeiffer | 250/370.09 |
| 6,030,119 A | 2/2000 | Tachibana et al. | |
| 6,042,267 A | 3/2000 | Muraki et al. | |
| 6,320,934 B1 | 11/2001 | Carroll et al. | |
| 6,652,141 B1 * | 11/2003 | Cianciosi | 378/191 |
| 7,973,250 B2 * | 7/2011 | Groeller et al. | 174/481 |
| 2006/0115715 A1 * | 6/2006 | Ge et al. | 429/97 |

* cited by examiner

*Primary Examiner* — Hoon Song
(74) *Attorney, Agent, or Firm* — Drinker Biddle & Reath LLP

(57) ABSTRACT

An intraoral sensor 1 includes: a case 4 having a first plate-shaped portion 12 and a second plate-shaped portion 16 that face each other; a photodetecting element 34 contained in the case 4 so that a light incident surface faces the first plate-shaped portion 12; a cover 6a, arranged on the outer surface of the second plate-shaped portion 16, for covering an opening 16a; and fixing members 32a and 32b, arranged between the second plate-shaped portion 16 and the cover 6a, for fixing to the case 4 a signal cable 24 connected to the photodetecting element 34 extending via the opening 16a from the inside to the outside of the case 4. This enables improvement of a connection strength between the case of the imaging device and the signal cable extending from an opposite side of the imaging surface.

15 Claims, 15 Drawing Sheets

*Fig.10*
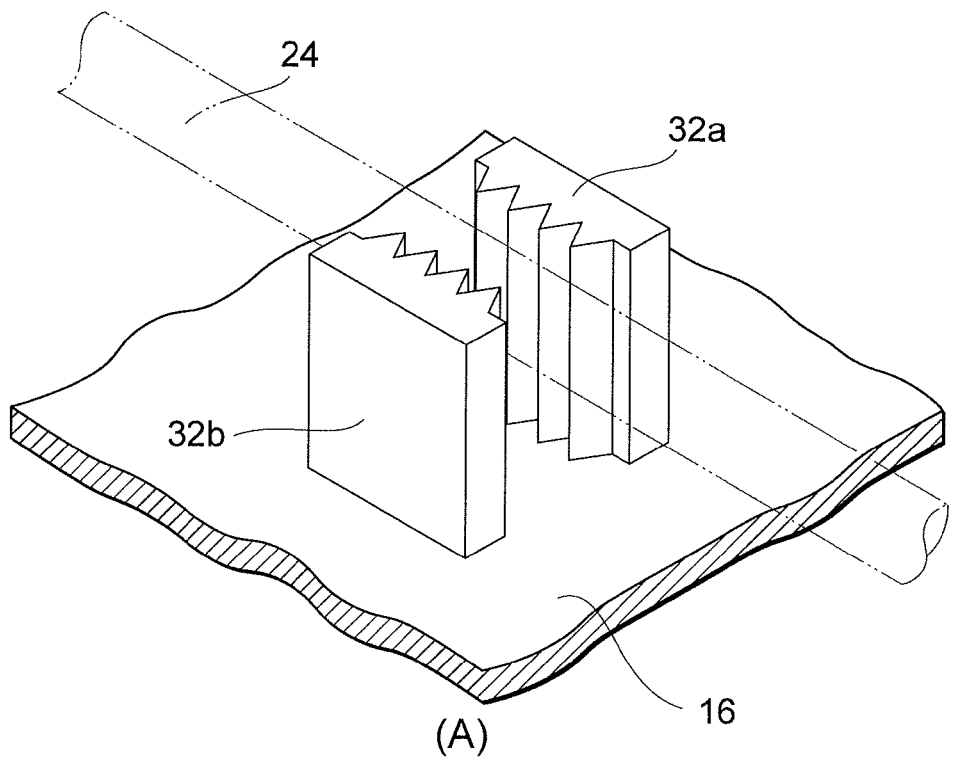
(A)
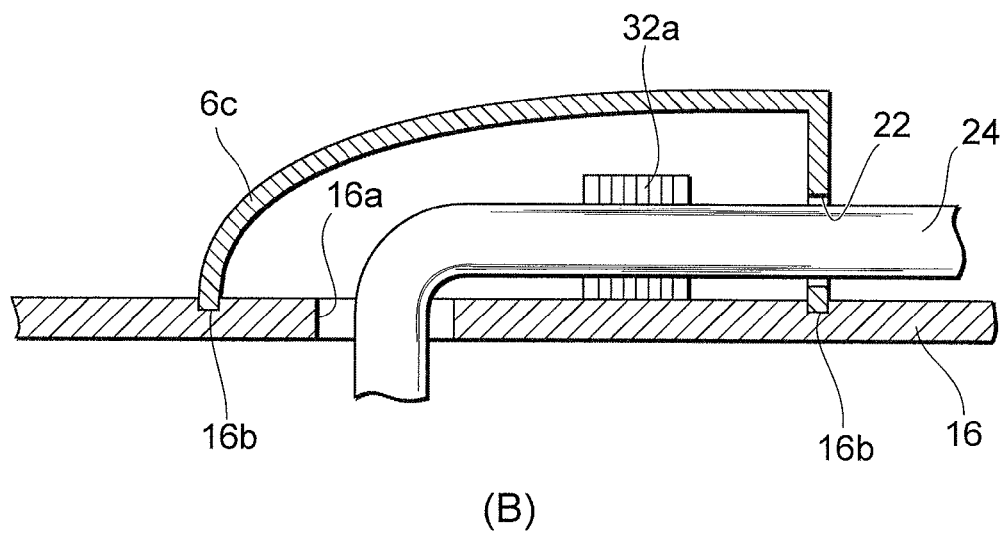
(B)

Fig.11
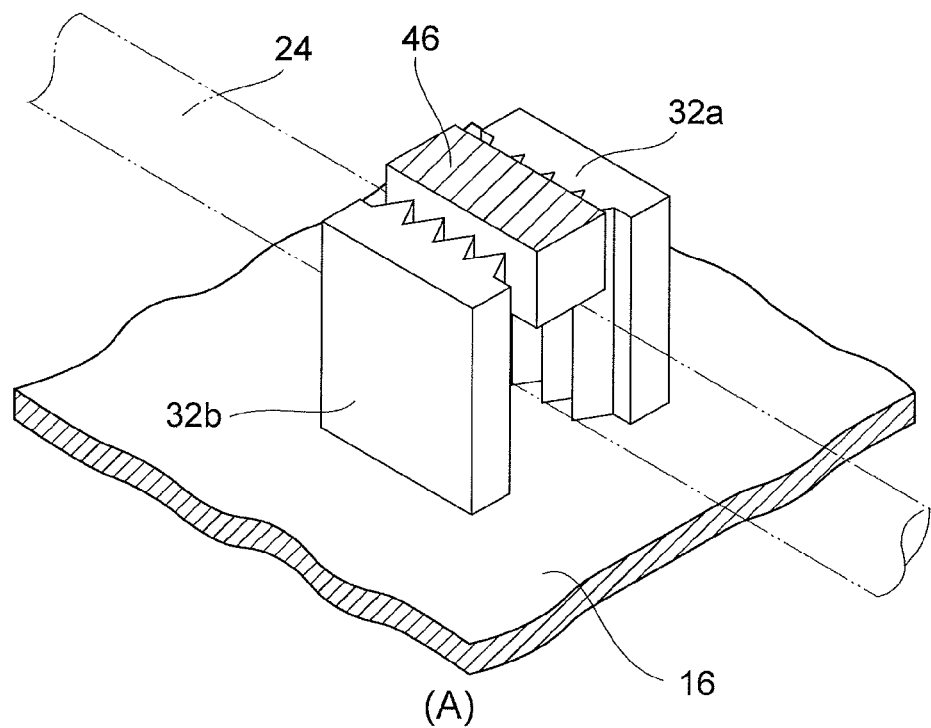
(A)
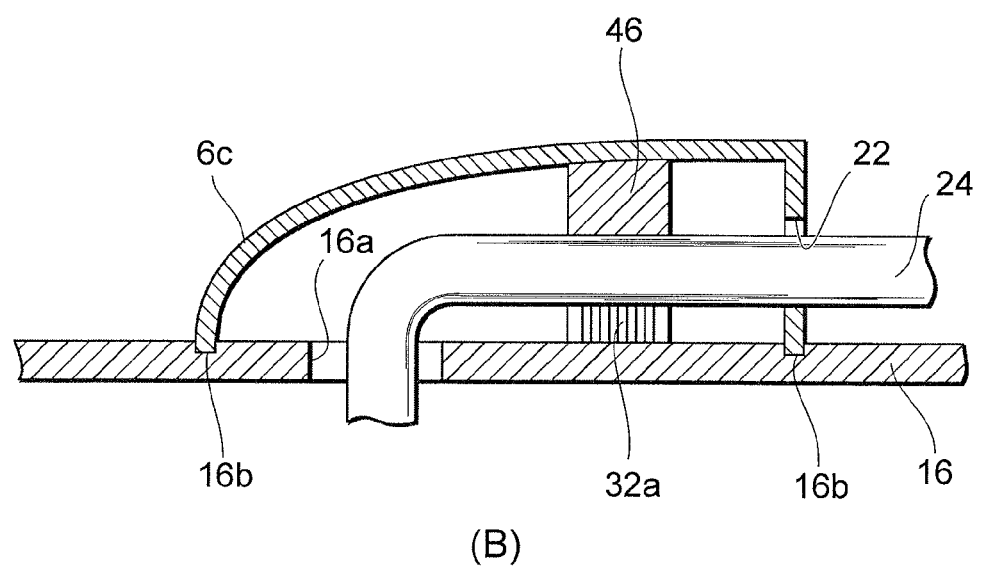
(B)

*Fig.12*
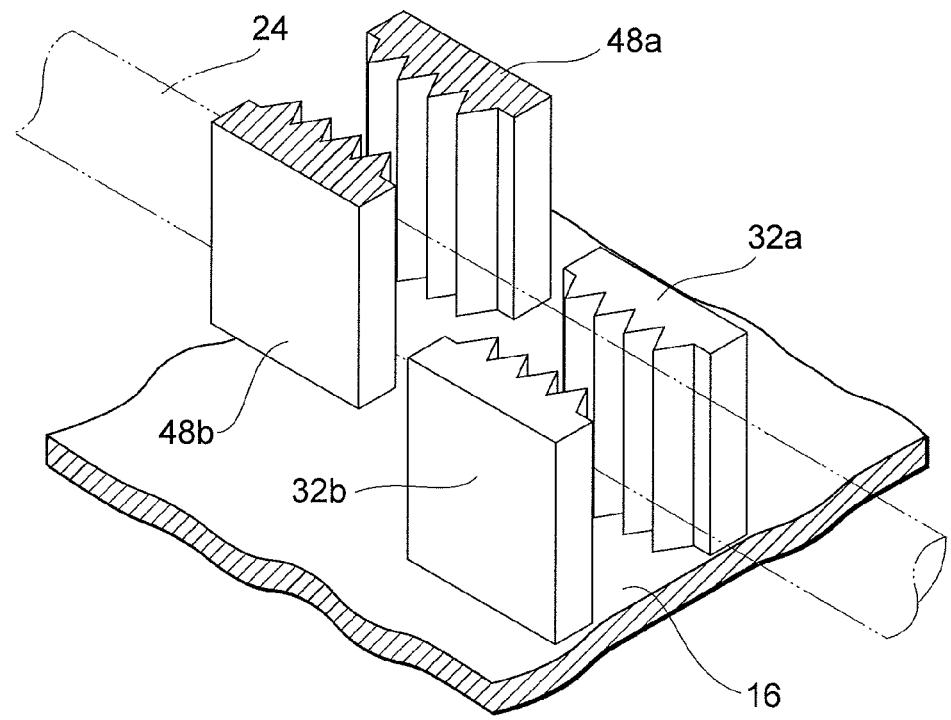
(A)
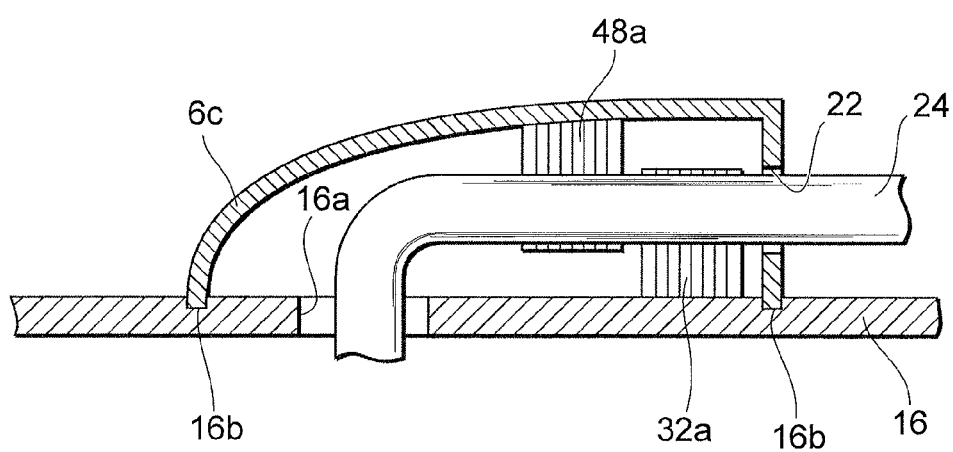
(B)

*Fig.13*
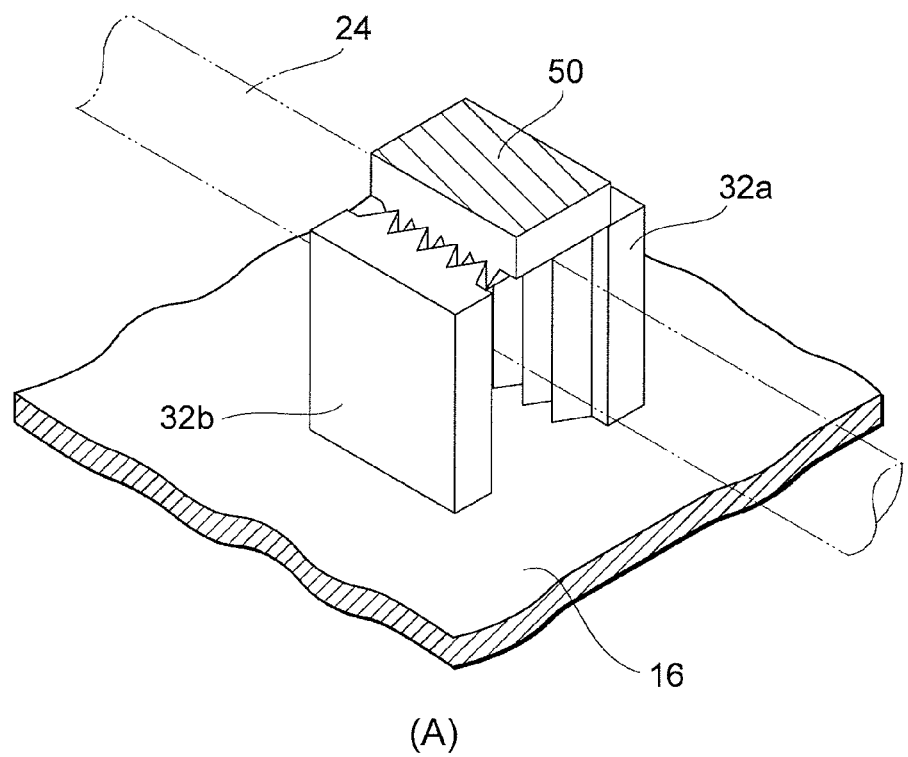
(A)
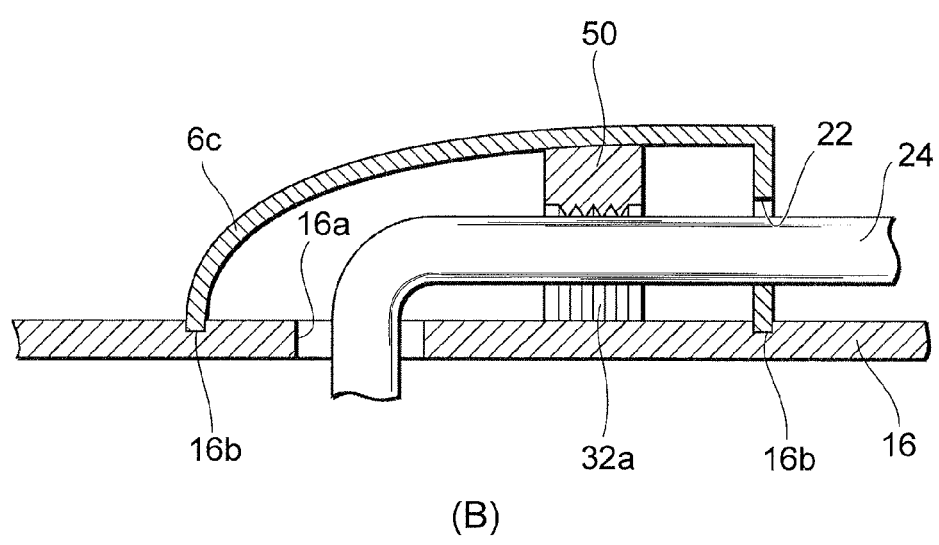
(B)

Fig.14
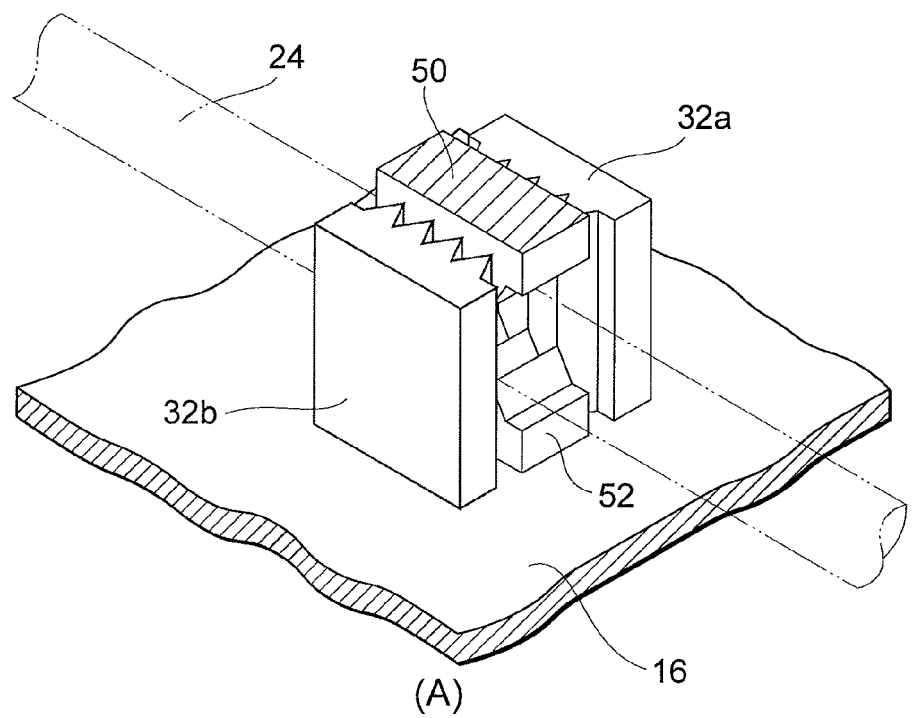
(A)
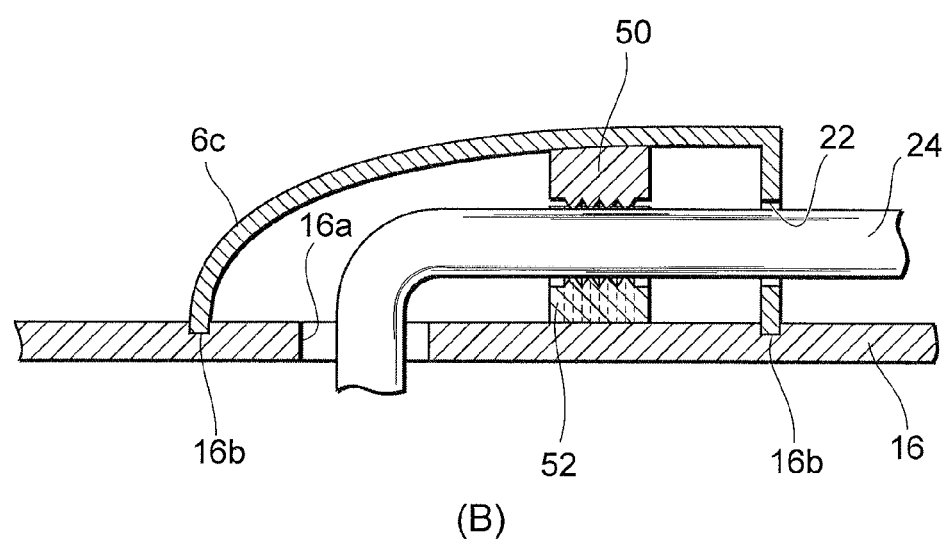
(B)

Fig.15
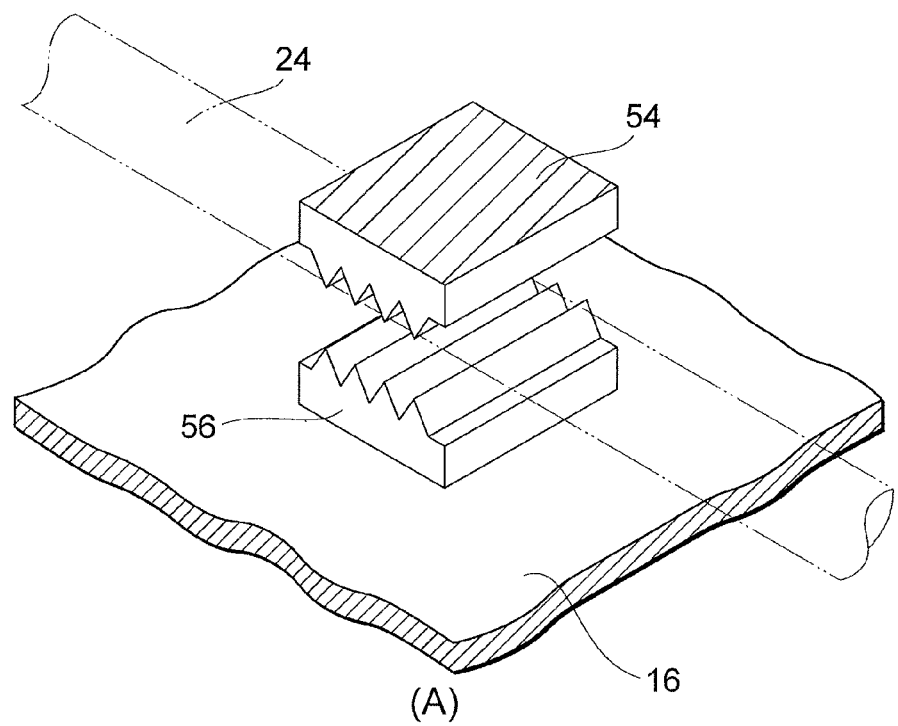
(A)
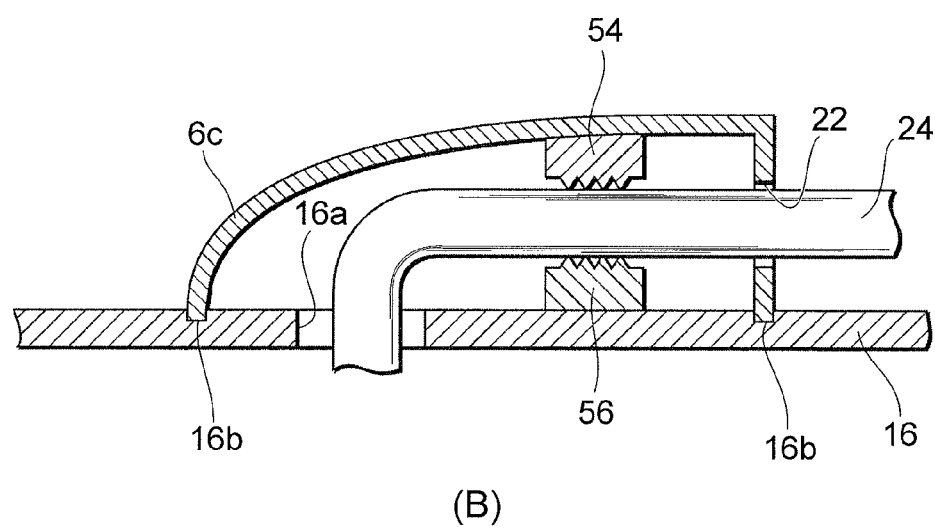
(B)

IMAGING DEVICE

TECHNICAL FIELD

The present invention relates to an imaging device, inserted into an oral cavity, for imaging teeth, etc.

BACKGROUND ART

Patent Documents 1 to 3 disclose imaging devices for photographing teeth, etc., in an oral cavity. In the case of an intraoral sensor in Patent Document 1, a signal cable is connected to a circuit board on the rear side of an imaging surface. In the case of an X-ray image sensor in Patent Document 2, a signal cable extends via a capsule, a bobbin, etc., on the rear side of an imaging surface. In the case of an intraoral sensor in Patent Document 3, a signal cable is connected to a circuit board on the rear side of an imaging surface via a cap, a sleeve, etc.
Patent Document 1: U.S. Pat. No. 6,652,141
Patent Document 2: U.S. Pat. No. 6,320,934
Patent Document 3: U.S. Pat. No. 5,691,539

DISCLOSURE OF THE INVENTION

Problems to be Solved by the Invention

In all the sensors described above, the signal cable extends from an opposite side of the imaging surface on which to receive imaging light. Thus, when the sensor is inserted into the oral cavity, the number of opportunities for which the signal cable comes into contact with the oral cavity is decreased, and as a result, discomfort that a patient feels at the time of photographing the oral cavity can be suppressed. However, in the sensor in which the signal cable thus extends from the opposite side of the imaging surface, the discomfort felt by the patient is decreased, and at the same time, the strength for the tension or bending of the signal cable is decreased. Therefore, due to the bending or tension of the signal cable, there is a possibility in such a sensor that a problem occurs to an electrical connection between the signal cable and the sensor.

Therefore, an object of the present invention is to improve a connection strength between a package of an imaging device and a signal cable extending from an opposite side of an imaging surface.

Means for Solving the Problems

An imaging device according to the present invention includes: a package having a case including a first plate-shaped portion and a second plate-shaped portion facing the first plate-shaped portion, and a cover, arranged on an outer surface of the second plate-shaped portion, for covering an opening formed in the second plate-shaped portion; a photodetecting element having a light incident surface and being contained in the case so that the light incident surface faces the first plate-shaped portion; and a fixing unit, arranged between the second plate-shaped portion and the cover, for fixing to the package a signal cable connected to the photodetecting element extending via the opening from the inside to the outside of the case.

According to the present invention, when the signal cable is pulled out from the opposite side of the photodetecting surface, the signal cable is fixed to the package by the fixing unit. In this way, the signal cable is fixed to the package by the fixing unit, and thus, even when there is bending or tension for the signal cable, it is possible to avoid a situation where a problem occurs to the electrical connection with the signal cable.

Effect of the Invention

According to the imaging device of the present invention, it is possible to improve a connection strength between a package of an imaging device and a signal cable extending from an opposite side of an imaging surface.

BRIEF DESCRIPTION OF THE DRAWINGS

FIG. 10 is a diagram showing a structure of a fixing unit according to the embodiment.
FIG. 11 is a diagram showing a structure of the fixing unit according to the embodiment.
FIG. 12 is a diagram showing a structure of the fixing unit according to the embodiment.
FIG. 13 is a diagram showing a structure of the fixing unit according to the embodiment.
FIG. 14 is a diagram showing a structure of the fixing unit according to the embodiment.
FIG. 15 is a diagram showing a structure of the fixing unit according to the embodiment.

DESCRIPTION OF THE SYMBOLS 1, 1*a*, 1*b*, 1*c*, 1*d*—Intraoral sensor, 10—Second case member, 12—First plate-shaped portion, 14—First side-wall member, 14*a*, 18*a*—End portion, 16—Second plate-shaped portion, 16*a*—Opening, 16*b*—Fitting groove, 18—Second side-wall member, 2, 2*a*, 2*b*, 2*c*, 2*d*—Package, 20—Side-wall portion, 22—Hole portion, 24—Signal cable, 26*a*, 26*b*, 30*a*, 30*b*, 38*a*, 38*b*—Protrusion, 28*a*, 28*b*—Projected piece, 32*a*, 32*b*, 46, 48*a*, 48*b*, 50, 52, 54, 56—Fixing member, 34—Photodetector, 34*a*—Scintillator, 34*c*—Circuit board, 34*b*—Image sensor, 35—Light incident surface, 36—Pad, 4—Case, 40*a*—Skirt portion, 41*a*, 43*a*, 45*a*, 47*a*—Bolt hole, 42*a*—Bolt, 44*a*—Spacer, 6, 6*a*, 6*c*, 6*d*, 6*b*—Cover, 8—First case member.

BEST MODES FOR CARRYING OUT THE INVENTION

Hereinafter, with reference to drawings, a preferable embodiment according to the present invention will be described in detail. In the description of the drawings, where possible, same components are denoted by same reference symbols, and overlapping descriptions will be omitted.

Figure 1:
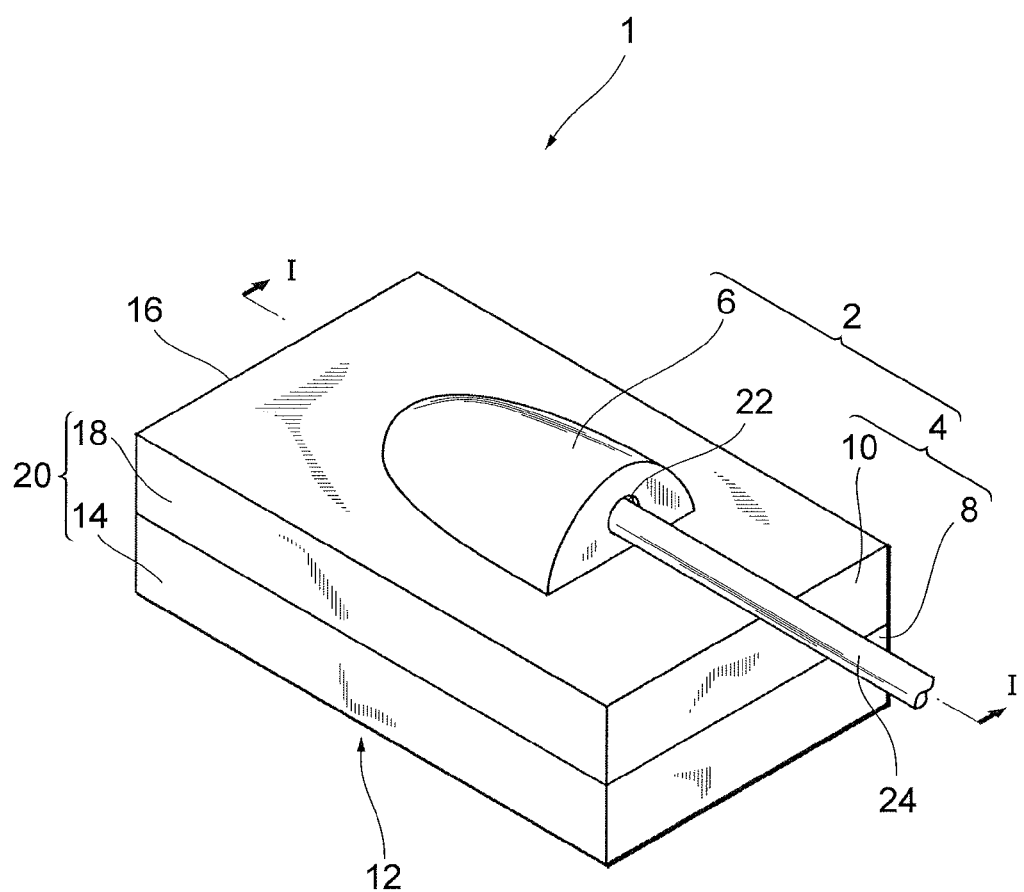
FIG. 1 is a diagram showing an appearance of an intraoral sensor according to an embodiment.

FIG. 1 shows an appearance of an intraoral sensor 1 according to an embodiment. The intraoral sensor 1 is an imaging device, inserted into an oral cavity of a patient, for imaging an X-ray image of teeth, etc., in an oral cavity. The intraoral sensor 1 is connected to a signal cable 24 extending from a control device for controlling the intraoral sensor 1. The intraoral sensor 1 is provided with a package 2. The package 2 includes a first plate-shaped portion 12 and a second plate-shaped portion 16 spaced and facing each other, and a side-wall portion 20 extending between the peripheral edge of the first plate-shaped portion 12 and the peripheral edge of the second plate-shaped portion 16. The side-wall portion 20 includes a first side-wall member 14 extending from the peripheral edge of the first plate-shaped portion 12 and a second side-wall member 18 extending from the peripheral edge of the second plate-shaped portion 16. In the second plate-shaped portion 16, an opening 16a (for example, see FIG. 2, etc.) formed through a case 4 from the outside to the inside is provided.

The package 2 includes the case 4 and a cover 6. The case 4 includes a first case member 8 and a second case member 10. The first case member 8 includes the first plate-shaped portion 12 and the first side-wall member 14. The second case member 10 includes the second plate-shaped portion 16 and the second side-wall member 18.

The intraoral sensor 1 includes the cover 6. The cover 6 is arranged on the outer surface of the second plate-shaped portion 16. The cover 6 covers the opening 16a (for example, see FIG. 2, etc.). The cover 6 includes a hole portion 22, and the hole portion 22 is formed through the cover 6 from the outside to the inside. The signal cable 24 extends from the outside to the inside of the cover 6 via the hole portion 22, and extends, via the opening 16a, from the inside of the cover 6 (outside of the case 4) to the inside of the case 4. The signal cable 24 is connected to a photodetecting element 34 arranged within the case 4 (for example, see FIG. 2, etc.). Here, the X-ray is incident on the first plate-shaped portion 12, and the signal cable 24 is pulled out from the side of the second plate-shaped portion 16 opposite (on the back surface side of) the first plate-shaped portion 12 on which the X-ray is incident.

The intraoral sensor 1 includes a fixing unit for fixing the signal cable 24 to the case 4. The fixing unit is arranged between the second plate-shaped portion 16 and the cover 6, fixes to the package 2 the signal cable 24 extending, via the opening 16a, from the inside to the outside of the case 4. Specific examples of the fixing unit are shown in FIG. 10 to FIG. 15, and will be described in detail later. It is noted that in FIG. 2 to FIG. 9, the fixing unit (a fixing member 32a and a fixing member 32b) shown in FIG. 10 is described as an example.

Figure 2:
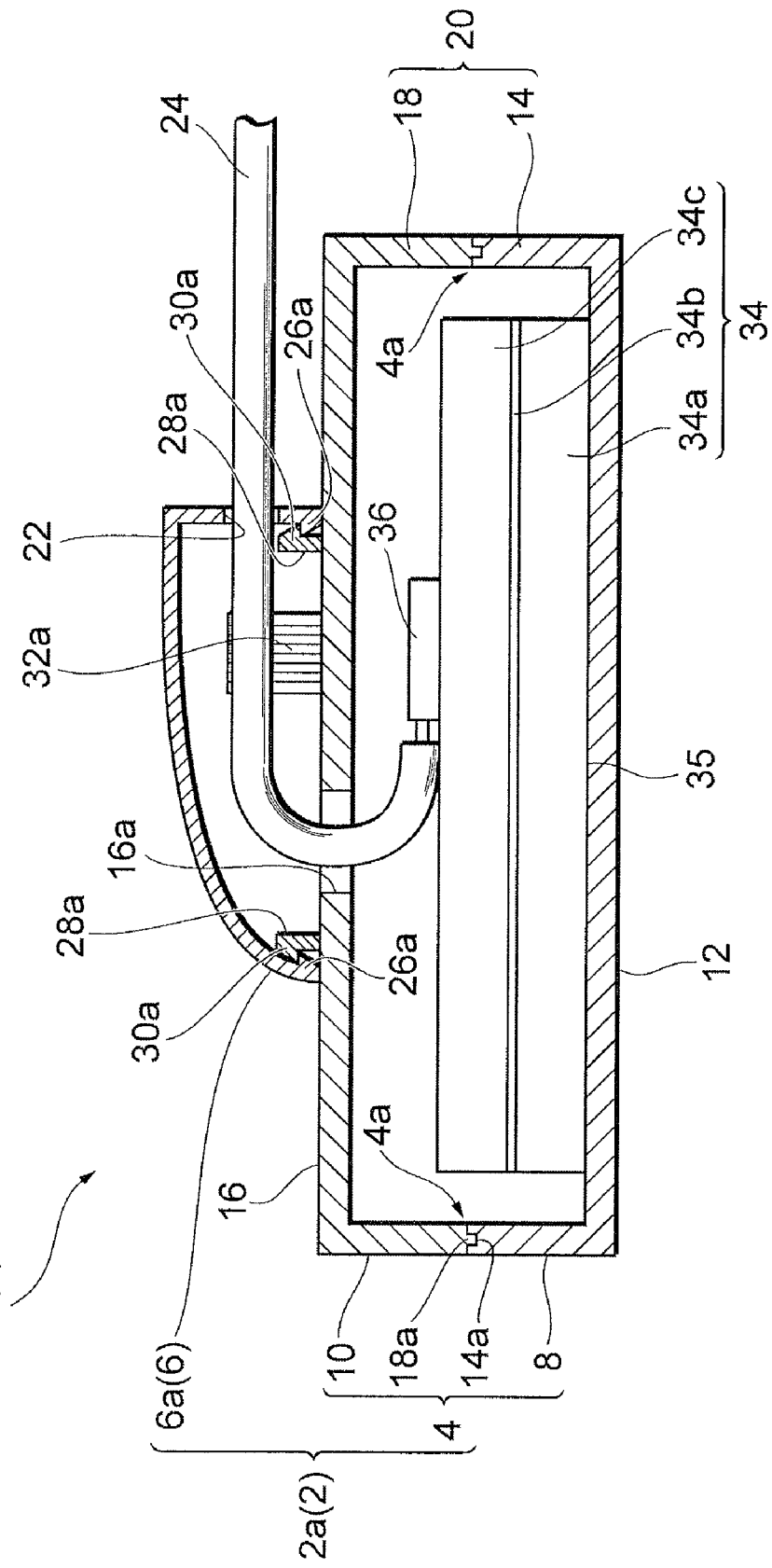
FIG. 2 is a diagram showing a cross-sectional structure of the intraoral sensor according to the embodiment.
Figure 3:
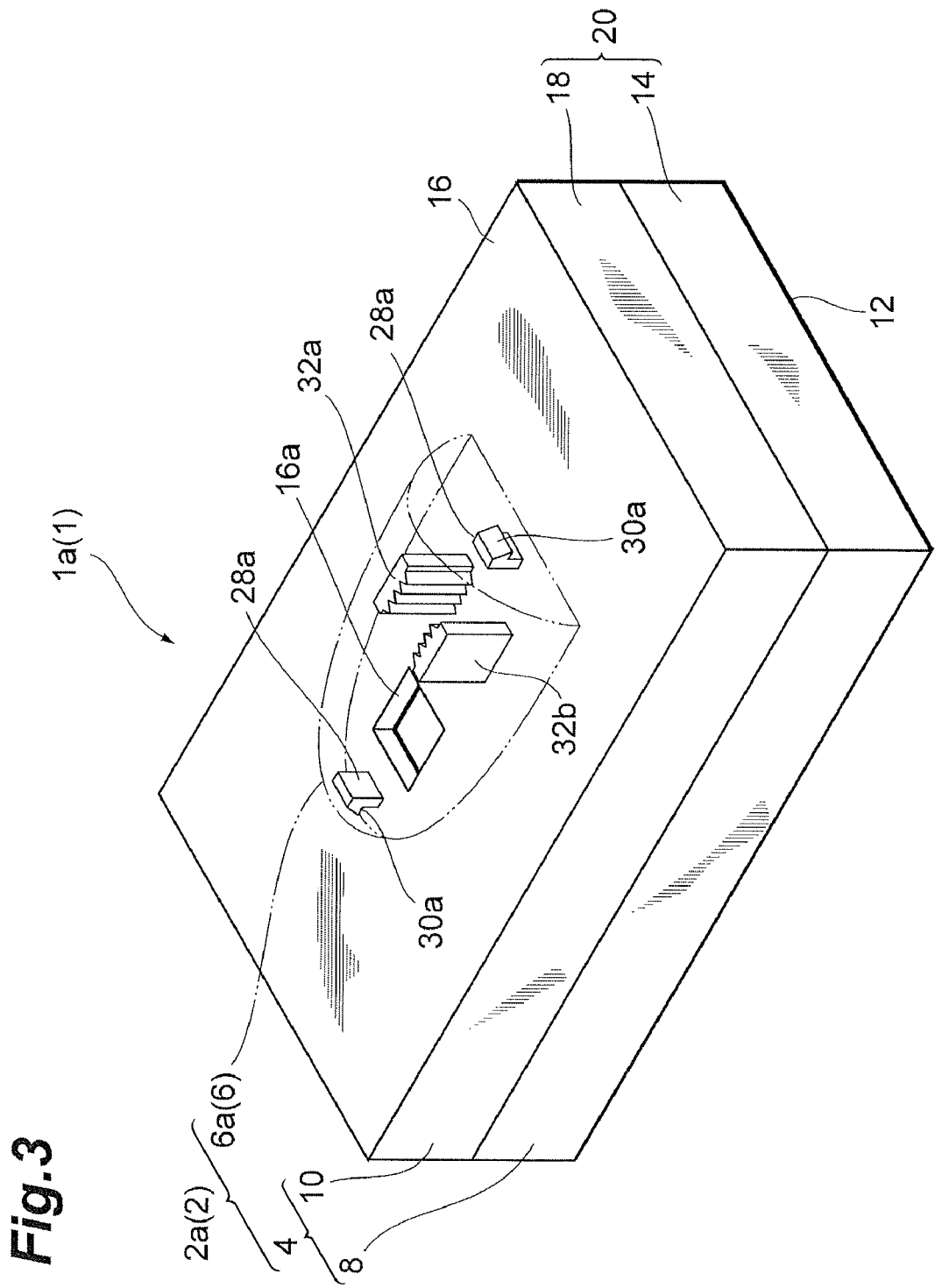
FIG. 3 is a perspective view of the intraoral sensor according to the embodiment.
Figure 4:
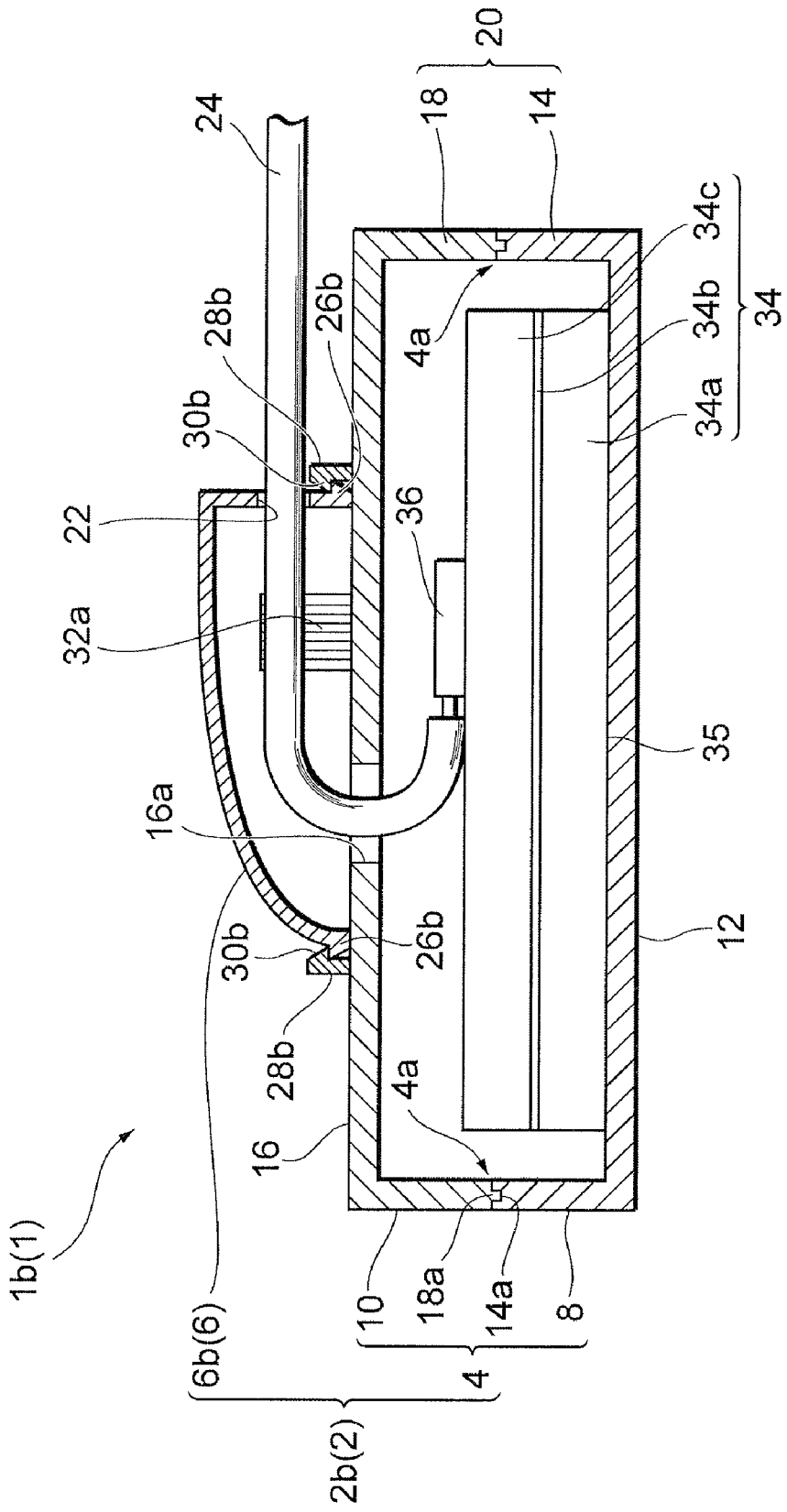
FIG. 4 is a diagram showing a cross-sectional structure of the intraoral sensor according to the embodiment.
Figure 5:
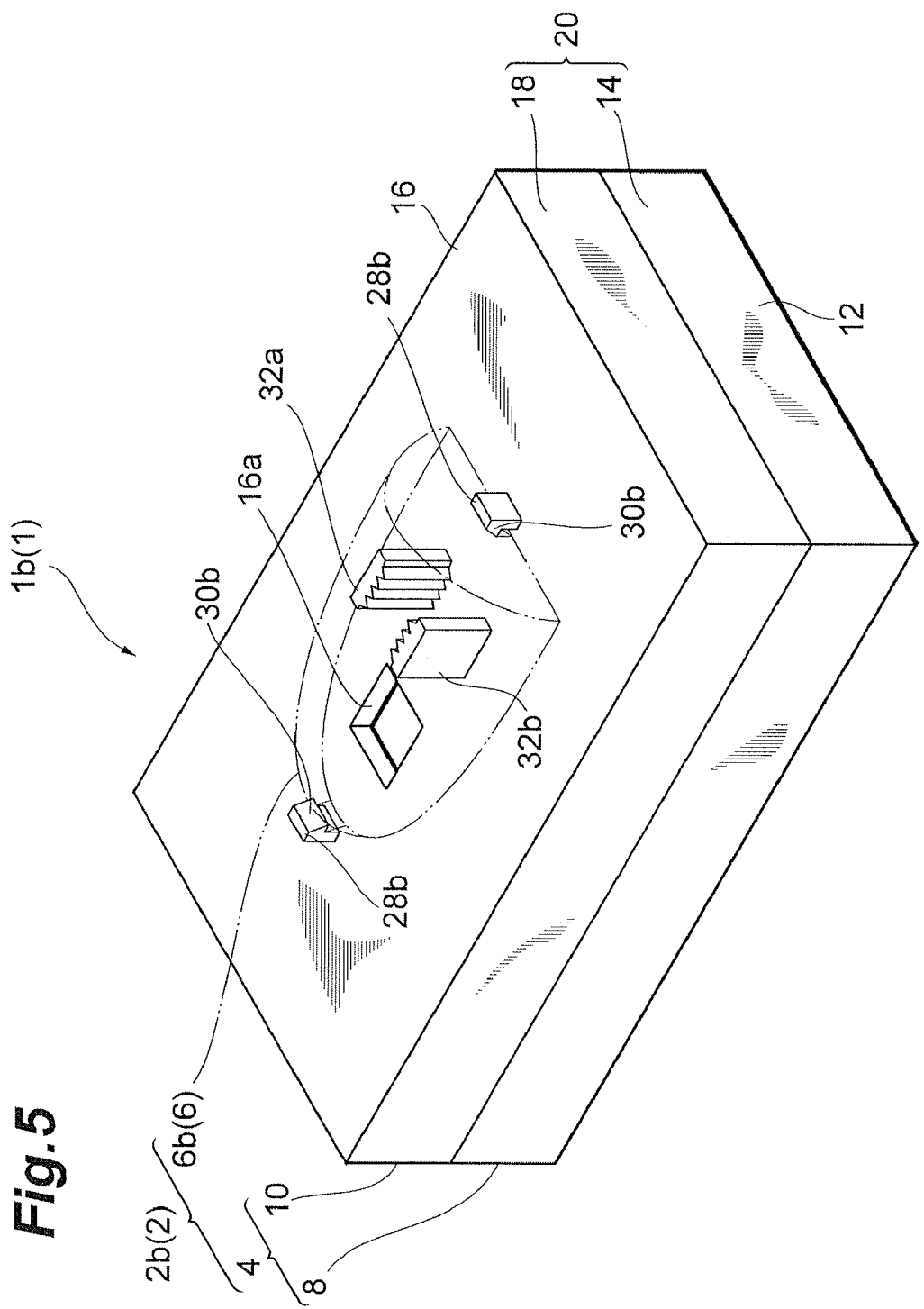
FIG. 5 is a perspective view of the intraoral sensor according to the embodiment.
Figure 6:
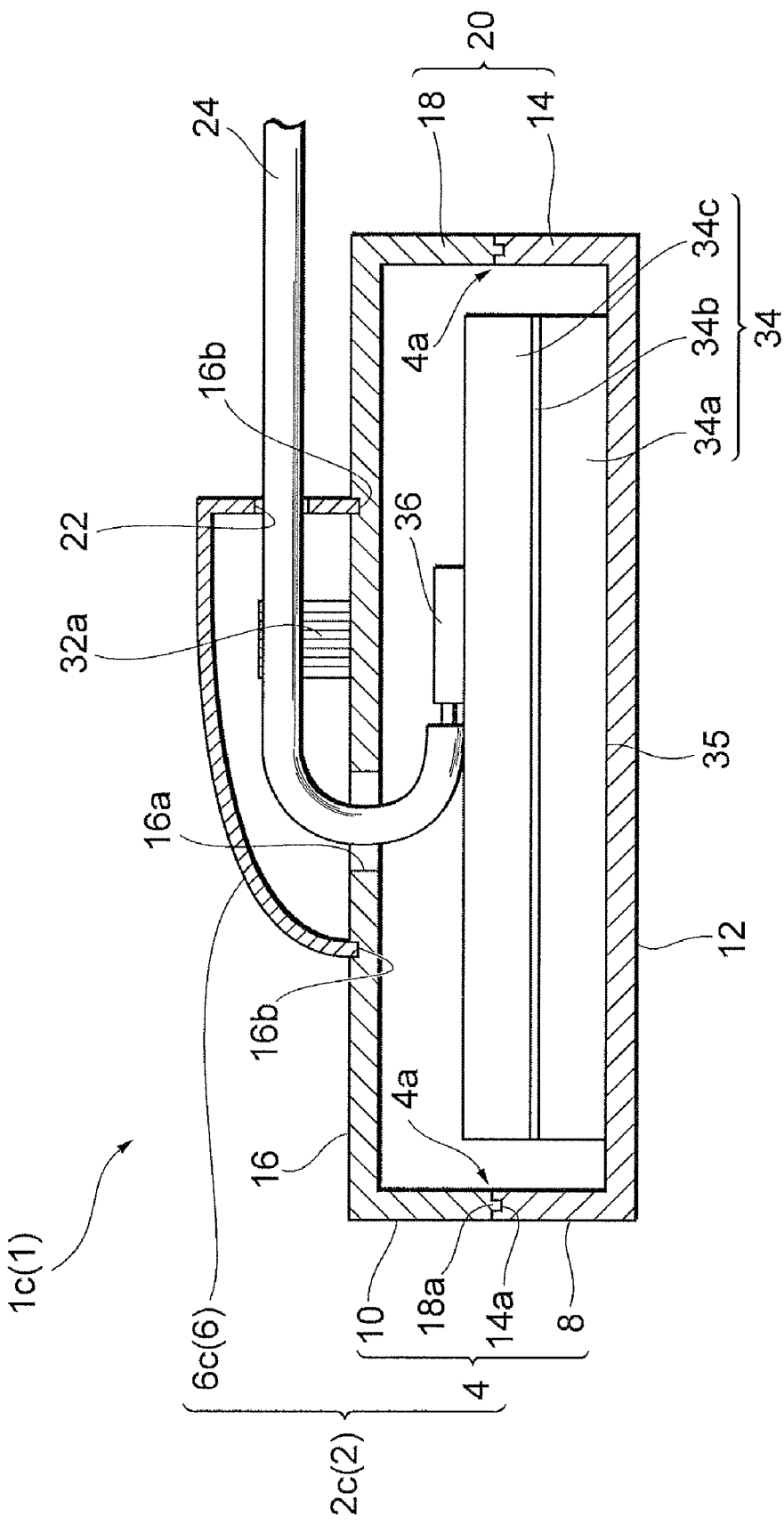
FIG. 6 is a diagram showing a cross-sectional structure of the intraoral sensor according to the embodiment.
Figure 7:
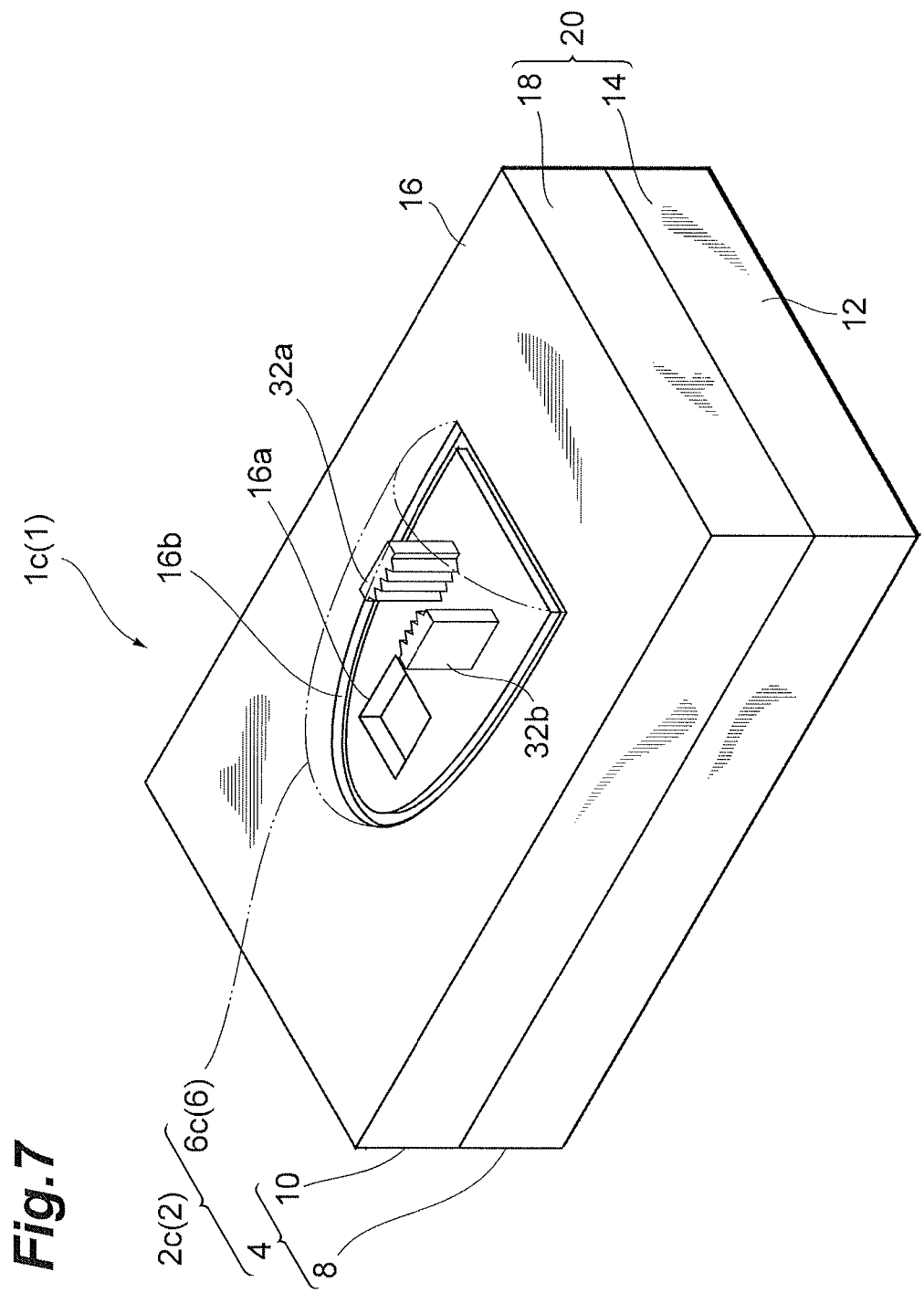
FIG. 7 is a perspective view of the intraoral sensor according to the embodiment.
Figure 8:
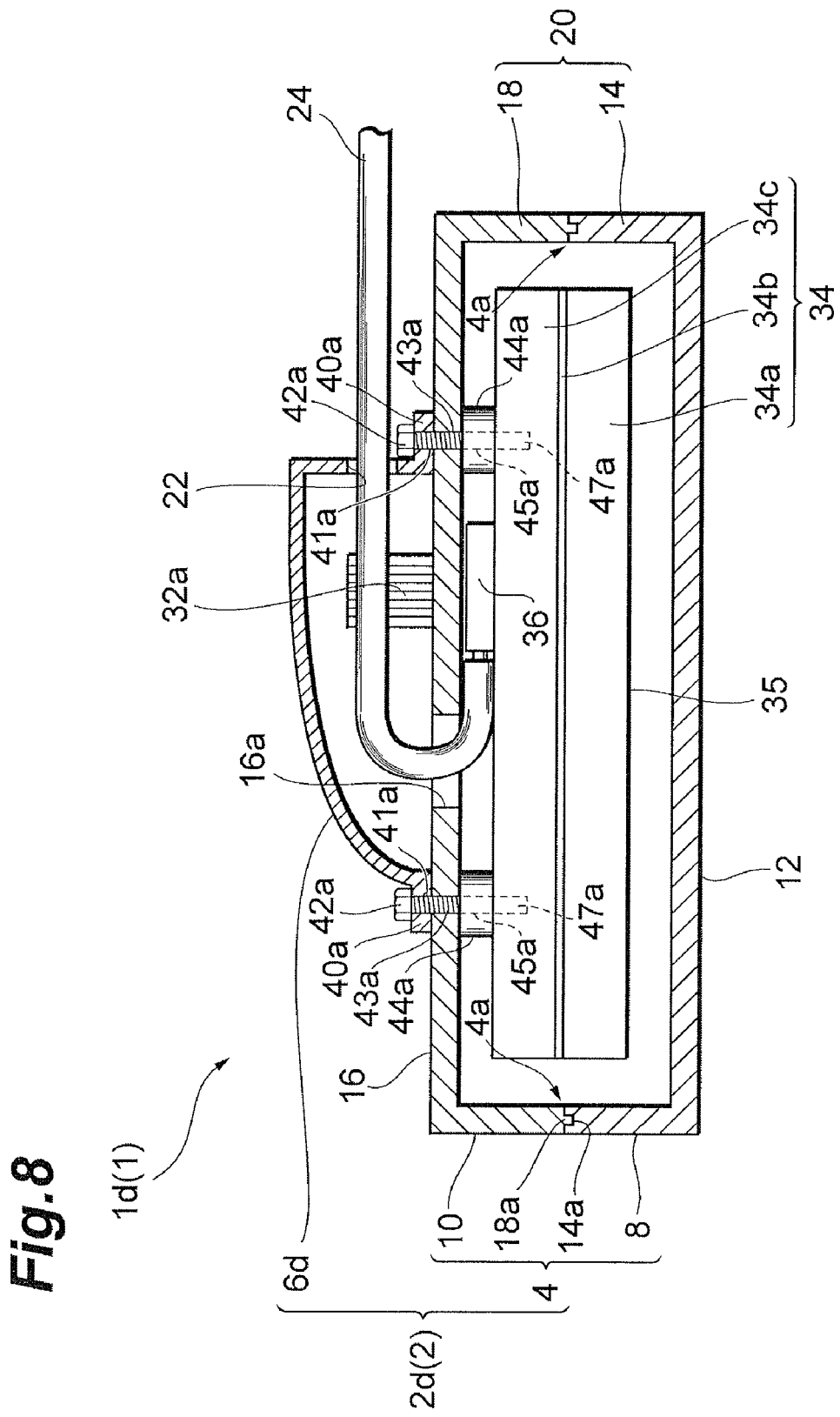
FIG. 8 is a diagram showing a cross-sectional structure of the intraoral sensor according to the embodiment.
Figure 9:
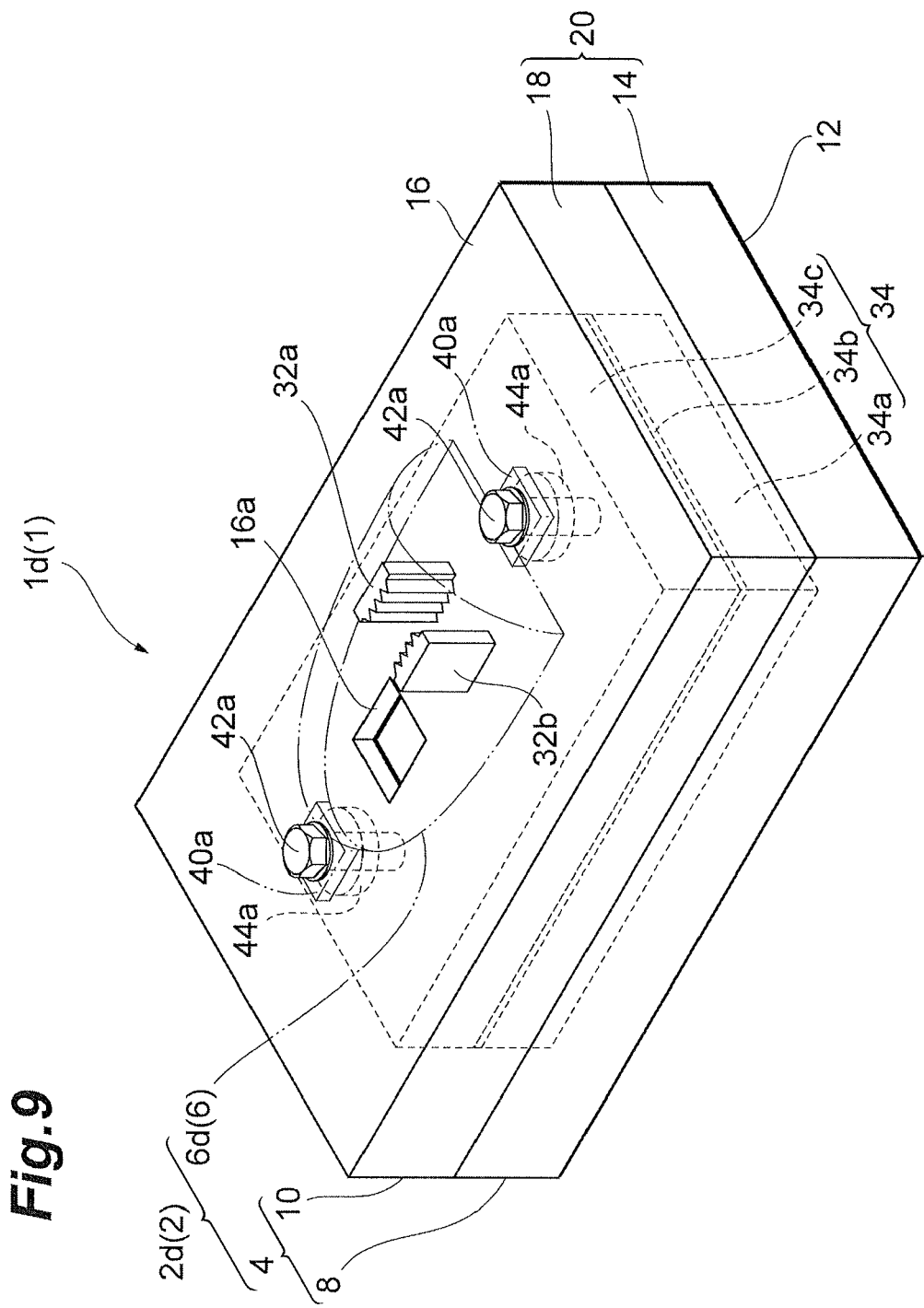
FIG. 9 is a perspective view of the intraoral sensor according to the embodiment.

Next, a specific configuration of the intraoral sensor 1 will be described. As specific examples of the intraoral sensor 1, an intraoral sensor 1a to an intraoral sensor 1d, respectively shown in FIG. 2 to FIG. 9, will be described. The configuration of the intraoral sensor 1a is shown in FIG. 2 and FIG. 3, the configuration of the intraoral sensor 1b is shown in FIG. 4 and FIG. 5, the configuration of the intraoral sensor 1c is shown in FIG. 6 and FIG. 7, and the configuration of the intraoral sensor 1d is shown in FIG. 8 and FIG. 9. FIG. 2, FIG. 4, FIG. 6, and FIG. 8 are diagrams showing cross-sectional structures of the intraoral sensor 1 (the intraoral sensor 1a to the intraoral sensor 1d) along a line I-I shown in FIG. 1, and FIG. 3, FIG. 5, FIG. 7, and FIG. 9 are perspective views respectively showing the intraoral sensor 1a to the intraoral sensor 1d.

First, with reference to FIG. 2 to FIG. 9, the configuration common to the intraoral sensor 1a to the intraoral sensor 1d will be described. The intraoral sensor 1a to the intraoral sensor 1d include the photodetecting element 34. The photodetecting element 34 is an element for converting an X-ray image into an electrical image signal and outputting it via the signal cable 24, and is contained in the case 4. The photodetecting element 34 includes a scintillator 34a for converting the X-ray image into visible light, an image sensor 34b for converting the visible light from the scintillator 34a into an electrical image signal, and a circuit board 34c for loading the image signal from the image sensor 34b.

The scintillator 34a has a light incident surface 35 on which the X-ray is incident. The image sensor 34b is arranged on the scintillator 34a on the opposite side of the light incident surface 35. The circuit board 34c is arranged on the image sensor 34b. On the circuit board 34c, a pad 36 (or solder) is provided, and the pad 36 electrically connects an electrical circuit of the circuit board 34c to the signal cable 24. The photodetecting element 34 is contained in the case 4 so that the light incident surface 35 of the scintillator 34a faces the first plate-shaped portion 12 and the circuit board 34c faces the second plate-shaped portion 16.

Inside of the cover 6 (a cover 6a to a cover 6d) and on the outer surface of the second plate-shaped portion 16, a fixing unit formed by the fixing member 32a and the fixing member 32b is arranged. Here, the cover 6a to the cover 6d are specific examples of the cover 6. It is noted that the fixing units arranged in the intraoral sensor 1a to the intraoral sensor 1d are not limited thereto, and any one of the fixing units described in FIG. 10 to FIG. 15 may be adoptable.

A joint portion between the first case member 8 and the second case member 10, i.e., an end portion 14a of the first side-wall member 14 and an end portion 18a of the second side-wall member 18 that come into contact with each other, are fittingly inserted as indicated by reference symbol 4a in the drawing. As a result, the first case member 8 and the second case member 10 are joined without misalignment. It is noted that the first case member 8 and the second case member 10 may be fittingly inserted via resin, etc.

Next, with reference to FIG. 2 and FIG. 3, a feature of the intraoral sensor 1a will be described. The intraoral sensor 1a includes a package 2a and projected pieces 28a. The package 2a includes the cover 6a and the case 4. The package 2a and the cover 6a are examples of the package 2 and the cover 6, respectively. The cover 6a includes an end portion that comes into contact with the outer surface of the second plate-shaped portion 16 and a plurality of (in this embodiment, two) protrusions 26a provided at the end portion. The protrusions 26a are protruded toward the side covered with the cover 6a (inside of the cover 6a).

The projected pieces 28a are arranged on the outer surface of the second plate-shaped portion 16 inside of the cover 6a and at the positions corresponding to those of the protrusions 26a, and the number of projected pieces to be arranged is equal to that of the protrusions 26a (in this embodiment, two). The two projected pieces 28a are placed to face each other with the opening 16a being sandwiched therebetween. At the ends of the projected pieces 28a, the protrusions 30a are formed. The protrusions 30a are protruded toward the opposite sides of directions in which the engaged protrusions 26a protrude, and thus, the protrusions 30a are engaged with the protrusions 26a. As a result of the protrusions 30a being engaged with the protrusions 26a, the cover 6a is held with the case 4.

Next, with reference to FIG. 4 and FIG. 5, a feature of the intraoral sensor 1b will be described. The intraoral sensor 1b includes a package 2b and projected pieces 28b. The package 2b includes the cover 6b and the case 4. The package 2b and the cover 6b are examples of the package 2 and the cover 6, respectively. The cover 6b includes an end portion that comes into contact with the outer surface of the second plate-shaped portion 16 and a plurality of (in this embodiment, two) protrusions 26b provided at the end portion. The protrusions 26b are protruded to the side opposite (outside of the cover 6b) the side (inside of the cover 6b) covered with the cover 6b.

The projected pieces 28b are arranged on the outer surface of the second plate-shaped portion 16 outside of the cover 6b and at the positions corresponding to those of the protrusions 26b, and the number of projected pieces to be arranged is equal to that of the protrusions 26b (in this embodiment, two). The two projected pieces 28b are placed to face each other with the opening 16a being sandwiched therebetween. At the ends of the projected pieces 28b, the protrusions 30b are formed. The protrusions 30b are protruded toward the opposite sides of directions in which the engaged protrusions 26b protrude, and thus, the protrusions 30b are engaged with the protrusions 26b. As a result of the protrusions 30b being engaged with the protrusions 26b, the cover 6b is held with the case 4.

Next, with reference to FIG. 6 and FIG. 7, a feature of the intraoral sensor 1c will be described. The intraoral sensor 1c is provided with a package 2c. The package 2c includes the cover 6c and the case 4. The package 2c and the cover 6c are examples of the package 2 and the cover 6, respectively. The cover 6c includes an end portion that comes into contact with the second plate-shaped portion 16, and on the outer surface of the second plate-shaped portion 16, a fitting groove 16b is formed along the end portion of the cover 6c. The opening 16a, the fixing member 32a, and the fixing member 32b are placed within a region surrounded by the fitting groove 16b on the outer surface of the second plate-shaped portion 16. The end portion of the cover 6c is (for example, via resin, etc.) fitted into the fitting groove 16b. In this way, as a result of the end portion of the cover 6c being fitted into the fitting groove 16b (for example, via resin, etc.), the cover 6c is held with the case 4.

Next, with reference to FIG. 8 and FIG. 9, a feature of the intraoral sensor 1d will be described. The intraoral sensor 1d includes a package 2d, a plurality of bolts 42a, and a plurality of spacers 44a. The package 2d includes the cover 6d and the case 4. The package 2d and the cover 6d are examples of the package 2 and the cover 6, respectively. In the cover 6d, a plurality of (in this embodiment, two) skirt portions 40a are provided at the end portion that comes into contact with the outer surface of the second plate-shaped portion 16. It is noted that the cover 6d may optionally include the single skirt portion extending along the end portion that comes into contact with the outer surface of the second plate-shaped portion 16.

Each of the skirt portions 40a has a plate shape extending from the cover 6d along the outer surface of the second plate-shaped portion 16, and comes into contact with the outer surface. The skirt portion 40a protrudes like a plate shape, on the side opposite the side covered with the cover 6d (outside of the cover 6d). The spacers 44a are arranged between the circuit board 34c and the second plate-shaped portion 16. The number of spacers 44a to be arranged is equal to that of the skirt portions 40a (in this embodiment, two).

Each skirt portion 40a is placed on the spacer 44a via the second plate-shaped portion 16.

In the skirt portions 40a, the second plate-shaped portion 16, the spacers 44a, and the circuit board 34c, bolt holes into which bolts 42a are screwed are respectively provided. The bolt holes include bolt holes 41a formed in the skirt portions 40a, bolt holes 43a formed in the second plate-shaped portion 16, bolt holes 45a formed in the spacers 44a, and bolt holes 47a formed in the circuit board 34c. The bolt hole 41a is a through hole in the skirt portion 40a, the bolt hole 43a is a through hole in the second plate-shaped portion 16, and the bolt hole 45a is a through hole in the spacer 44a. The bolt hole 47a is a concave depression formed in the circuit board 34c, and has a bottom wall inside thereof.

The number of bolt holes 41a, 43a, 45a, and 47a, and bolts 42a to be arranged are equal to that of the skirt portions 40a (in this embodiment, two). The bolt holes 43a, 45a, and 47a are provided at positions corresponding to those of the bolt holes 41a (where overlapping with the bolt holes 41a as seen from the top of the second plate-shaped portion 16), and the bolt holes 41a, 43a, 45a, and 47a are lined up in a straight line so that the bolts 42a are screwed from the bolt holes 41a. Into a single bolt hole including a set of bolt holes 41a, 43a, 45a, and 47a lined up in a straight line, one bolt 42a is screwed. In this way, by means of a bolt fixing using the bolts 42a, the cover 6d and the photodetecting element 34 are held with the case 4.

Next, a specific configuration of the fixing unit for fixing the signal cable 24 to the case 4 will be described. FIG. 10 to FIG. 15 show specific examples of the fixing unit. It is noted that the cover 6 shown in FIG. 10 to FIG. 15 is the cover 6c and the package 2 is the package 2c (see FIG. 6), however, this is not always the case and the cover may be any one of the covers 6a to 6d and the package may be any one of the packages 2a to 2d.

First, the fixing unit shown in FIG. 10 will be described. (A) in FIG. 10 is a perspective view showing the fixing unit, and (B) in FIG. 10 is a diagram showing a cross-sectional structure of the intraoral sensor along the line I-I in FIG. 1. The fixing unit shown in FIG. 10 includes the fixing member 32a (first fixing member) and the fixing member 32b (second fixing member). The fixing members 32a and 32b are arranged, in a manner to sandwich the signal cable 24, to face each other on the outer surface of the second plate-shaped portion 16. The fixing members 32a and 32b have a plate shape and are similar in dimension.

Out of a plurality of surfaces provided in the fixing member 32a, on a surface facing the fixing member 32b (surface that comes into contact with the signal cable 24), and out of surfaces provided in the fixing member 32b, on a surface facing the fixing member 32a (surface that comes into contact with the signal cable 24), a plurality of grooves are respectively formed. The plurality of grooves extend parallel to one another toward the upper side of the second plate-shaped portion 16. By means of the plurality of grooves, a plurality of depressed and protruded portions are configured in each of the fixing members 32a and 32b, and by the plurality of depressed and protruded portions provided in the fixing members 32a and 32b, the signal cable 24 is effectively sandwiched between the fixing member 32a and the fixing member 32b. Due to the function of sandwiching the signal cable 24 by the fixing members 32a and 32b, the signal cable 24 becomes capable of being firmly fixed to the package 2c.

Next, the fixing unit shown in FIG. 11 will be described. (A) in FIG. 11 is a perspective view showing the fixing unit, and (B) in FIG. 11 is a diagram showing a cross-sectional structure of the intraoral sensor along the line I-I in FIG. 1.

The fixing unit shown in FIG. 11 includes the fixing member 32a, the fixing member 32b, and a fixing member 46 (third fixing member). The fixing member 46 is arranged on the inner surface of the cover 6c, and placed between the fixing member 32a and the fixing member 32b. It is preferable that the width of the fixing member 46 be smaller than the diameter of the signal cable 24. The width of the fixing member 46 is the dimension of the fixing member 46 along a direction perpendicular to a direction in which the signal cable 24 extends.

Between the fixing member 32a and the fixing member 32b, the fixing member 46 comes into contact with the signal cable 24 and presses the signal cable 24 against the side of the second plate-shaped portion 16. Due to the function of sandwiching the signal cable 24 by the fixing members 32a and 32b, and the function of pressing the same by the fixing member 46 against the side of the second plate-shaped portion 16, the signal cable 24 becomes capable of being firmly fixed to the package 2c.

The fixing unit shown in FIG. 12 will be described. (A) in FIG. 12 is a perspective view showing the fixing unit, and (B) in FIG. 12 is a diagram showing a cross-sectional structure of the intraoral sensor along the line I-I in FIG. 1. The fixing unit shown in FIG. 12 includes the fixing member 32a, the fixing member 32b, a fixing member 48a (fourth fixing member), and a fixing member 48b (fifth fixing member). The fixing members 48a and 48b are arranged, in a manner to sandwich the signal cable 24, on the inner surface of the cover 6c. The fixing members 48a and 48b have a plate shape and are similar in dimension.

Out of a plurality of surfaces provided in the fixing member 48a, on a surface facing the fixing member 48b (surface that comes into contact with the signal cable 24), and out of surfaces provided in the fixing member 48b, on a surface facing the fixing member 48a (surface that comes into contact with the signal cable 24), a plurality of grooves are respectively formed. The plurality of grooves extend parallel to one another toward the upper side of the second plate-shaped portion 16. By means of the plurality of grooves, a plurality of depressed and protruded portions are configured in each of the fixing members 48a and 48b, and by the plurality of depressed and protruded portions provided in the fixing members 48a and 48b, the signal cable 24 is effectively sandwiched between the fixing member 48a and the fixing member 48b. Due to the function of sandwiching the signal cable 24 by the fixing members 48a and 48b, the signal cable 24 becomes capable of being firmly fixed to the package 2c.

Moreover, the fixing members 48a and 32a are sequentially placed along a direction in which the signal cable 24 extends from the opening 16a, and also the fixing members 48b and 32b are sequentially placed along this direction. The fixing members 48a and 48b first sandwich and hold the signal cable 24 extending from the opening 16a, and the fixing members 32a and 32b further sandwich and hold the signal cable 24 extending from the fixing members 48a and 48b. Therefore, due to the function of sandwiching the signal cable 24 by the fixing members 48a and 48b, and the function of sandwiching the signal cable 24 by the fixing members 32a and 32b, the signal cable 24 becomes capable of being more firmly fixed to the package 2c.

It is noted that a configuration in which the position of the fixing members 48a and 48b is replaced by the position of the fixing members 32a and 32b may be optionally adopted. Moreover, a configuration in which only the fixing members 48a and 48b are arranged without the fixing members 32a and 32b may also be adopted.

Next, the fixing unit shown in FIG. 13 will be described. (A) in FIG. 13 is a perspective view showing the fixing unit, and (B) in FIG. 13 is a diagram showing a cross-sectional structure of the intraoral sensor along the line I-I in FIG. 1. The fixing unit shown in FIG. 13 includes the fixing member 32a, the fixing member 32b, and a fixing member 50 (third fixing member). The fixing member 50 is arranged on the inner surface of the cover 6c, and placed between the fixing member 32a and the fixing member 32b. It is preferable that the width of the fixing member 50 be smaller than the diameter of the signal cable 24. The width of the fixing member 50 is the dimension of the fixing member 50 along a direction perpendicular to a direction in which the signal cable 24 extends.

Between the fixing member 32a and the fixing member 32b, the fixing member 50 comes into contact with the signal cable 24 and presses the signal cable 24 against the side of the second plate-shaped portion 16. Out of a plurality of surfaces provided in the fixing member 50, on a surface facing the second plate-shaped portion 16 (surface that comes into contact with the signal cable 24), a plurality of grooves are formed. The plurality of grooves extend parallel to one another along a direction from the fixing member 32a toward the fixing member 32b. By means of the plurality of grooves, a plurality of depressed and protruded portions are configured, and by the plurality of depressed and protruded portions provided in the fixing member 50, the signal cable 24 is effectively pressed against the side of the second plate-shaped portion 16. Due to the function of sandwiching the signal cable 24 by the fixing members 32a and 32b, and the function of pressing the same by the fixing member 50 against the side of the second plate-shaped portion 16, the signal cable 24 becomes capable of being firmly fixed to the package 2c.

Next, the fixing unit shown in FIG. 14 will be described. (A) in FIG. 14 is a perspective view showing the fixing unit, and (B) in FIG. 14 is a diagram showing a cross-sectional structure of the intraoral sensor along the line I-I in FIG. 1. The fixing unit shown in FIG. 14 includes the fixing member 32a, the fixing member 32b, the fixing member 50, and a fixing member 52 (sixth fixing member). The fixing member 52 is arranged on the outer surface of the second plate-shaped portion 16, and placed between the fixing member 32a and the fixing member 32b. It is preferable that the width of the fixing member 52 be smaller than the diameter of the signal cable 24. The width of the fixing member 52 is the dimension of the fixing member 52 along a direction perpendicular to a direction in which the signal cable 24 extends.

Between the fixing member 32a and the fixing member 32b, the fixing member 52 comes into contact with the signal cable 24, and the signal cable 24 is sandwiched by the fixing member 50 and the fixing member 52. Out of a plurality of surfaces provided in the fixing member 52, on a surface facing the fixing member 50 (surface that comes into contact with the signal cable 24), a plurality of grooves are formed. The plurality of grooves extend parallel to one another along a direction from the fixing member 32a toward the fixing member 32b. By means of the plurality of grooves, a plurality of depressed and protruded portions are configured, and by the plurality of depressed and protruded portions provided in the fixing member 52, the signal cable 24 is effectively sandwiched between the fixing member 50 and the fixing member 52. Due to the function of sandwiching the signal cable 24 by the fixing members 32a and 32b, and the function of sandwiching the signal cable 24 by the fixing members 50 and 52, the signal cable 24 becomes capable of being firmly fixed to the package 2c.

Next, the fixing unit shown in FIG. 15 will be described. (A) in FIG. 15 is a perspective view showing the fixing unit, and (B) in FIG. 15 is a diagram showing a cross-sectional structure of the intraoral sensor along the line I-I in FIG. 1. The fixing unit shown in FIG. 15 includes a fixing member 54 (seventh fixing member) and a fixing member 56 (eighth fixing member). The fixing member 54 is arranged on the inner surface of the cover 6c, and the fixing member 56 is arranged on the outer surface of the second plate-shaped portion 16. As seen from above the outer surface of the second plate-shaped portion 16, the fixing member 54 and the fixing member 56 are placed in an overlapping manner. The fixing member 54 and the fixing member 56 sandwich the signal cable 24.

Out of a plurality of surfaces provided in the fixing member 54, on a surface facing the fixing member 56 (surface that comes into contact with the signal cable 24), a plurality of grooves are formed. Out of a plurality of surfaces provided in the fixing member 56, on a surface facing the fixing member 54 (surface that comes into contact with the signal cable 24), a plurality of grooves are formed. The grooves in the fixing members 54 and 56 are oriented toward the same direction, and oriented perpendicularly to the direction in which the signal cable 24 extends between the fixing members 54 and 56. By means of the plurality of grooves, depressed and protruded portions are configured in each of the fixing members 54 and 56, and by the plurality of depressed and protruded portions provided in the fixing members 54 and 56, the signal cable 24 is effectively sandwiched between the fixing member 54 and the fixing member 56. Due to the function of sandwiching the signal cable 24 by the fixing members 54 and 56, the signal cable 24 becomes capable of being firmly fixed to the package 2c.

It is noted that the orientations of the respective grooves in the fixing members 32a, 32b, 48a, 48b, 50, 52, 54, and 56 are not limited to those shown in FIG. 10 to FIG. 15, and may be optionally directed perpendicularly to those orientations, for example.

Here, the imaging device of the embodiment is configured to include: a package having a case including a first plate-shaped portion and a second plate-shaped portion facing the first plate-shaped portion, and a cover, arranged on the outer surface of the second plate-shaped portion, for covering an opening formed through the second plate-shaped portion; a photodetecting element having a light incident surface and being contained in the case so that the light incident surface faces the first plate-shaped portion; and a fixing unit, arranged between the second plate-shaped portion and the cover, for fixing to the package a signal cable connected via the opening to the photodetecting element extending from the inside to the outside of the case.

It is preferable in the imaging device that the case has a first case member including the first plate-shaped portion and a second case member including the second plate-shaped portion, and an end portion of the first case member and an end portion of the second case member that come into contact with each other are fittingly inserted. In this way, because the first case member and the second case member are joined through fitted insertion, it becomes possible to avoid a situation where a joint portion between the first case member and the second case member is misaligned.

It is preferable that the imaging device further includes a plurality of projected pieces arranged on the outer surface of the second plate-shaped portion, the cover includes a plurality of protrusions, the number of which is equal to that of the projected pieces, at positions corresponding to those of the projected pieces, and the plurality of protrusions are engaged with the plurality of projected pieces, respectively. In this way, the plurality of projected pieces arranged on the second plate-shaped portion and the plurality of protrusions arranged in the cover are engaged with one another, and thus, the cover is firmly held with the case.

It is preferable in the imaging device that a groove is formed in a portion that comes into contact with the cover, out of the outer surface of the second plate-shaped portion, and the cover is fitted in the groove. In this way, on the surface of the case, the groove is provided, and as a result of the cover being fitted in the groove, the cover and the case are joined. Therefore, the configuration of the cover and the case becomes simple, thereby facilitating the fabrication.

It is preferable that the imaging device further includes a plurality of bolts, the cover includes a plurality of skirt portions which come into contact with the outer surface of the second plate-shaped portion and the number of which is equal to that of the plurality of bolts, in the plurality of skirt portions, bolt holes are respectively provided, in the second plate-shaped portion and the circuit board, bolt holes are respectively provided at positions corresponding to those of the bolt holes of the skirt portions, and into the respective bolt holes of the skirt portions, the second plate-shaped portion, and the circuit board, the bolts are screwed. In this way, the cover and the case, and the circuit board and the case are bolted, and thus, the cover, the circuit board, and the case are capable of firmly being joined.

Preferably, in the imaging device, the fixing unit includes the first and second fixing members arranged in a manner to sandwich the signal cable on the outer surface of the second plate-shaped portion. In this way, the signal cable is capable of being sandwiched by the first and second fixing members, and thus, the signal cable becomes capable of being firmly fixed to the package.

Preferably, in the imaging device, the fixing unit further includes the third fixing member that is arranged on the inner surface of the cover and placed between the first and second fixing members. In this way, the signal cable is capable of being sandwiched by the first and second fixing members while being pressed by the third fixing member against the side of the case, and thus, the signal cable becomes capable of being firmly fixed to the package.

Preferably, in the imaging device, the fixing unit further includes the fourth and fifth fixing members arranged to face each other in a manner to sandwich the signal cable on the inner surface of the cover. In this way, the signal cable is capable of being sandwiched by the first and second fixing members and the fourth and fifth fixing members, and thus, the signal cable becomes capable of being firmly fixed to the package.

Preferably, in the imaging device, the fixing unit further includes the sixth fixing member that is arranged on the outer surface of the second plate-shaped portion and placed between the first and second fixing members. In this way, the signal cable is capable of being sandwiched by the first and second fixing members and the third and sixth fixing members, and thus, the signal cable becomes capable of being firmly fixed to the package.

Preferably, in the imaging device, the fixing unit includes the seventh fixing member arranged on the outer surface of the second plate-shaped portion and the eighth fixing member arranged on the inner surface of the cover in a manner to overlap the seventh fixing member. In this way, the signal cable is capable of being sandwiched by the seventh and eighth fixing members, and thus, the signal cable becomes capable of being firmly fixed to the package.

INDUSTRIAL APPLICABILITY

The present invention is capable of being used as an imaging device in which the connection strength between the package of the imaging device and the signal cable extending from the opposite side of the imaging surface is improved.

The invention claimed is:

1. An imaging device, comprising:
a package having a case including a first plate-shaped portion and a second plate-shaped portion facing the first plate-shaped portion, and a cover, arranged on an outer surface of the second plate-shaped portion, for covering an opening formed in the second plate-shaped portion;
a photodetecting element having a light incident surface and being contained in the case so that the light incident surface faces the first plate-shaped portion; and
a fixing unit, arranged between the second plate-shaped portion and the cover, for fixing to the package a signal cable connected to the photodetecting element extending via the opening from the inside to the outside of the case, wherein
the fixing unit includes first and second fixing members arranged to face each other in a manner to sandwich the signal cable on the outer surface of the second late-shaped portion.

2. The imaging device according to claim 1, wherein
the case has a first case member including the first plate-shaped portion and a second case member including the second plate-shaped portion, and
an end portion of the first case member and an end portion of the second case member that come into contact with each other are fittingly inserted.

3. The imaging device according to claim 1, further comprising a plurality of projected pieces arranged on the outer surface of the second plate-shaped portion, wherein
the cover includes a plurality of protrusions, the number of which is equal to that of the projected pieces, at positions corresponding to those of the projected pieces, and
the plurality of protrusions are respectively engaged with the plurality of projected pieces.

4. The imaging device according to claim 1, wherein
in a portion that comes into contact with the cover, out of the outer surface of the second plate-shaped portion, a groove is formed, and
the cover is fitted in the groove.

5. The imaging device according to claim 1, further comprising a plurality of bolts, wherein
the cover includes a plurality of skirt portions which come into contact with the outer surface of the second plate-shaped portion and the number of which is equal to that of the plurality of bolts,
in the plurality of skirt portions, bolt holes are respectively provided,
in the second plate-shaped portion and a circuit board of the photodetecting element, bolt holes are respectively provided at positions corresponding to those of the bolt holes of the skirt portions, and
into the respective bolt holes of the skirt portions, the second plate-shaped portion, and the circuit board, the bolts are screwed.

6. The imaging device according to claim 1, wherein
the fixing unit further includes a third fixing member that is arranged on an inner surface of the cover and placed between the first and second fixing members.

7. The imaging device according to claim 6, wherein
the fixing unit further includes a sixth fixing member that is arranged on the outer surface of the second plate-shaped portion and placed between the first and second fixing members.

8. The imaging device according to claim 1, wherein
the fixing unit includes fourth and fifth fixing members arranged in a manner to sandwich the signal cable on the inner surface of the cover.

9. The imaging device according to claim 1, wherein
on a surface of the first fixing member facing the second fixing member, and on a surface of the second fixing member facing the first fixing member, a plurality of grooves extending parallel to one another are respectively formed.

10. An imaging device, comprising:
a package having a case including a first plate-shaped portion and a second plate-shaped portion facing the first plate-shaped portion, and a cover, arranged on an outer surface of the second plate-shaped portion, for covering an opening formed in the second plate-shaped portion;
a photodetecting element having a light incident surface and being contained in the case so that the light incident surface faces the first plate-shaped portion; and
a fixing unit, arranged between the second plate-shaped portion and the cover, for fixing to the package a signal cable connected to the photodetecting element extending via the opening from the inside to the outside of the case, wherein
the fixing unit includes a seventh fixing member arranged on the outer surface of the second plate-shaped portion and an eighth fixing member arranged on the inner surface of the cover in a manner to overlap the seventh fixing member.

11. The imaging device according to claim 10, wherein
the case has a first case member including the first plate-shaped portion and a second case member including the second plate-shaped portion, and
an end portion of the first case member and an end portion of the second case member that come into contact with each other are fittingly inserted.

12. The imaging device according to claim 10, further comprising a plurality of projected pieces arranged on the outer surface of the second plate-shaped portion, wherein
the cover includes a plurality of protrusions, the number of which is equal to that of the projected pieces, at positions corresponding to those of the projected pieces, and
the plurality of protrusions are respectively engaged with the plurality of projected pieces.

13. The imaging device according to claim 10, wherein
in a portion that comes into contact with the cover, out of the outer surface of the second plate-shaped portion, a groove is formed, and
the cover is fitted in the groove.

14. The imaging device according to claim 10, further comprising a plurality of bolts, wherein
the cover includes a plurality of skirt portions which come into contact with the outer surface of the second plate-shaped portion and the number of which is equal to that of the plurality of bolts,
in the plurality of skirt portions, bolt holes are respectively provided,
in the second plate-shaped portion and a circuit board of the photodetecting element, bolt holes are respectively provided at positions corresponding to those of the bolt holes of the skirt portions, and into the respective bolt holes of the skirt portions, the second plate-shaped portion, and the circuit board, the bolts are screwed.

15. The imaging device according to claim 10, wherein
on a surface of the seventh fixing member facing the eighth fixing member, and on a surface of the eighth fixing member facing the seventh fixing member, a plurality of grooves extending parallel to one another are respectively formed.

* * * * *